(12) United States Patent
Hageman (10) Patent No.: US 8,501,676 B2
(45) Date of Patent: *Aug. 6, 2013

(54) PREPARATION FOR USE OF ASPARTATE FOR REGULATING GLUCOSE LEVELS IN BLOOD

(75) Inventor: Robert Johan Joseph Hageman, Wageningen (NL)

(73) Assignee: N.V. Nutricia, Zoetermeer (NL)

( * ) Notice: Subject to any disclaimer, the term of this patent is extended or adjusted under 35 U.S.C. 154(b) by 705 days.

This patent is subject to a terminal disclaimer.

(21) Appl. No.: 11/632,871

(22) PCT Filed: Jul. 18, 2005

(86) PCT No.: PCT/NL2005/000519
§ 371 (c)(1),
(2), (4) Date: Jul. 18, 2008

(87) PCT Pub. No.: WO2006/009437
PCT Pub. Date: Jan. 26, 2006

(65) Prior Publication Data
US 2008/0269117 A1    Oct. 30, 2008

Related U.S. Application Data

(60) Provisional application No. 60/588,793, filed on Jul. 19, 2004.

(30) Foreign Application Priority Data

Jul. 19, 2004  (EP) .................................. 04077100
Aug. 20, 2004  (EP) .................................. 04077359

(51) Int. Cl.
*A61K 38/02* (2006.01)
(52) U.S. Cl.
USPC ............................. 514/1.1; 530/300; 530/350
(58) Field of Classification Search
None
See application file for complete search history.

(56) References Cited

U.S. PATENT DOCUMENTS

| 5,550,146 A * | 8/1996 | Acosta et al. ................. 514/400 |
| 6,042,834 A | 3/2000 | Baraka |
| 6,060,446 A * | 5/2000 | Zaloga et al. ..................... 514/2 |
| 6,706,697 B1 | 3/2004 | Macdonald |
| 2003/0118663 A1 | 6/2003 | Chang |

FOREIGN PATENT DOCUMENTS

| EP | 0629350 A1 | 12/1994 |
| EP | 0758852 A1 | 2/1997 |
| EP | 0957692 A1 | 11/1999 |
| WO | 0137850 A2 | 5/2001 |
| WO | 03105605 A2 | 12/2003 |
| WO | 03105882 A1 | 12/2003 |
| WO | 2004023891 A1 | 3/2004 |

OTHER PUBLICATIONS

Merriem-Webster dictionary reference, 2 pages. 2010.*
Hans N. Englyst and John H. Cummings, "Non-Starch Polysaccharides (Dietary Fiber) and Resistant Starch", MRC Dunn Clinical Nutrition Centre, New Developments in Dietary Fiber, Plenum Press, New York, 1990, pp. 205-225.

* cited by examiner

Primary Examiner — Marsha Tsay
(74) Attorney, Agent, or Firm — The Webb Law Firm (57) ABSTRACT

The invention relates to the use of specific protein and/or peptide fractions having a high aspartate content for regulating plasma glucose concentrations and increasing insulin sensitivity in a mammal. The invention relates to a complete food fortified with aspartate equivalents as well as a supplement rich in aspartate equivalents that is given simultaneously with or even minutes up to an hour prior to the consumption of a meal comprising glucose. The nutritional or pharmaceutical composition contains at least one protein having a high aspartate content, preferably of soy or dairy origin, which is further enriched with aspartate equivalents from another protein and/or free aspartate equivalents. The protein fraction comprises glutamate equivalents in a weight ratio of aspartate equivalents to glutamate equivalents (asp:glu) between 0.41:1 and 5:1.

20 Claims, 2 Drawing Sheets

Fig 1

Fig 2

PREPARATION FOR USE OF ASPARTATE FOR REGULATING GLUCOSE LEVELS IN BLOOD

BACKGROUND OF THE INVENTION

1. Field of the Invention

The invention pertains to a preparation for use of specific protein and/or peptide fractions having a high aspartate content for regulating plasma glucose concentrations and increasing insulin sensitivity in a mammal.

2. Description of the Related Art

Hyperglycaemia is a metabolic state of the body wherein glucose levels in blood are increased compared to normal concentrations in blood of about 3.9-6.1 mMol/l (70-110 mg per 100 ml). In times of starvation or after consumption of high amounts of glucose, these normal values tend to be outside this range, but the mammalian body has several mechanisms available to maintain glucose homeostasis.

Persons suffering from abnormally high glucose levels after consumption of a source of glucose are defined to suffer from a "high post-prandial glucose response" or to be "glucose intolerant". Impaired glucose tolerance can result in increased glucose levels after fasting and is often associated with impaired glucose metabolism. Important examples can be found in persons that are diagnosed to suffer from the so-called metabolic syndrome or syndrome X, obesity and several types of diabetes, like type I, type II and gestational diabetes. Also persons that are under high emotional stress and patients that experienced severe trauma, surgery or that suffer from an acute illness, for example those that are accepted in the Intensive Care Units (ICU) in a hospital, demonstrate impaired capacity to control their blood glucose levels to levels below 6.1 mMol/l, which is probably due to the action of stress hormones like cortisol. Apart from these groups, also persons having certain types of inherited errors in metabolism, e.g. persons suffering from propionic academia, isovaleric academia, methylmalonic academia, oxoacid coenzyme A thiolase deficiency or deficiencies in the activity of other thiolases, and persons that have an underdeveloped metabolic system like young infants often experience periods with high post-prandial glucose levels in blood.

High post-prandial glucose responses can lead to a plurality of negative effects on health and body function, especially when it occurs for longer times or when it is associated with increased glucose levels after starvation. Examples of such negative effects are cardiovascular problems, both on a micro- and macrovascular level, problems with impaired eyesight, renal problems, neurological problems like neuropathy and cognitive impairment, increased sensitivity to infections like those caused by yeasts, metabolic problems, and more acute effects like polyuria and feelings of excessive thirst and hunger.

Insulin plays a critical role in the functioning of the body and in particular in the metabolism of glucose in the body. Contrary to glucagon, insulin increases the uptake of glucose by peripheral cells, like those in skeletal muscle, and fat tissue, and in liver, pancreas and cardiac muscle, and it decreases hepatic gluconeogenesis. Insulin is released by the pancreas after consumption of food, in particular of food that comprises a source of glucose or protein. The release of insulin can be imparted when the pancreas has been severely damaged, e.g. during diabetes type I or pancreatitis. This will after some time result in severe health problems, especially when the decreased postprandial release of insulin occurs in combination with a decreased sensitivity to insulin. Insulin that is released then does not lead to increased absorption of glucose by the cells, in particular by the peripheral cells in the body like the muscle cells. This is also called "insulin resistance".

Apart from diabetics there are many other groups of persons that suffer from insulin resistance, like many obese persons and persons that suffer from the metabolic syndrome. Also after severe trauma or surgery and during the severe stages of several diseases like cancer and AIDS, net insulin resistance is frequently observed. Insulin resistance leads to severe health problems, especially on the longer term, and increases morbidity and mortality risks in such patients.

Despite high systemic levels of glucose during hyperglycaemia, several tissues may still suffer from low levels of intracellular glucose. In order to maintain intracellular energy homeostasis, lipids or proteins will under such conditions be used as energy source. In cases wherein insufficient amounts of lipids or proteins are consumed, or in situations wherein body stores of lipids are not metabolised properly, catabolism of lean body mass occurs. During energy malnutrition severe complications may occur, especially when loss of lean body mass has progressed. Therefore a need exists for a nutritional product which increases insulin sensitivity in energy-malnourished persons, like those patients that experience severe diseases, persons who are strongly obese and/or in particular in the malnourished diabetic patient.

Neonates and in particular preterm babies often suffer from underdeveloped metabolic systems, which need to adapt in a short time to a new nutritional regimen. During the first few days and even weeks dramatic changes occur in their body for example with regard to expression of enzymes, organ capacity e.g. of the liver, pancreas, gut and kidneys and gut content. When nutritional practices are not adapted to their metabolic capabilities, disorders and diseases can be observed such as abnormally high or low levels of glucose in the blood.

In the Western world the prevalence of obesity and diabetes has been rising considerably over the last decades and even children have become susceptible to these diseases or disorders.

Many approaches have been described in the prior art to find nutritional products which prevent that glucose levels in plasma become too low but at the same time decrease postprandial glucose response and/or that decrease insulin resistance.

Nutritional products have been developed that decrease hyperglycemic response after consumption thereof. For example, the postprandial glucose response is claimed to be flattened by including a slowly digestible carbohydrate source, or the digestion rate is decreased by including fibres. Also, the glucose source can be replaced by another ingredient which releases alternative carbohydrates like fructose, which does not directly result in increased glucose levels in the blood after consumption. An example hereof is given in WO-A-03/105882. However, often the unique metabolic and physiological properties of glucose are not met adequately and these alternative carbohydrates, especially fructose, are suspected of having undesired side effects, especially at high dosages, like causing diarrhea, hyperuricaemia, imparting temporarily hepatic energy stores and causing an inflammatory response.

Another approach in the art is to adapt the protein composition in order to increase insulin release. In particular fortification with arginine, but also leucine, glycine or phenylalanine has been advocated for this purpose. The problem of insulin resistance is however not solved by this approach. The release of even more insulin challenges the already highly stressed pancreas and thus does not seem to be a very efficient approach. In addition, it is believed that the prevalence of high plasma levels of insulin during longer periods of time increases the risk of becoming obese and developing insulin resistance at a later age. This is particularly important for patients that suffer from problems with the pancreas and some specific problems with the liver, such as during diabetes type I, pancreatitis, cirrhosis and hepatitis.

Most commercially available complete nutritional products for diabetics have a protein fraction based on casein or soy. A better post-prandial glucose responses is especially attributed to soy-based products. Disadvantages of products in which the protein fraction is predominantly formed from soy is that the soy taste is not very appreciated and also provides a non-optimal amino acid profile to meet all requirements, e.g. on the amount of essential amino acids, for persons that suffer from hyperglycaemia, especially in case of a malnourished patient suffering from a low lean body mass and requiring strong anabolism during a prolonged period of time.

U.S. Pat. No. 6,706,697 discloses a diabetic and weight loss composition formulated as powder for preparing a drink comprising about 15 wt % fructose and 10 wt % insulin, and wherein the protein fraction of the drink is an organoleptically more acceptable combination of about 44 wt % isolated soy protein and 20 wt % milk protein isolate. Milk protein isolate has been defined as a spray dried, soluble casein and whey proteins isolated from fresh skim milk, wherein the combination of casein and whey proteins is obtained from simultaneous isolation of all proteins present in milk, yielding a mixture of casein and whey of 80:20, providing about 8 wt % of aspartate equivalents. Disadvantageously, the use of high amounts of fructose as suggested in U.S. Pat. No. 6,706,697 may result in the aforementioned unwanted side effects.

US 2004/0043013 discloses a composition of agents for metabolic uncoupling therapy comprising one or more members of at least 4 groups of agents. Examples 3-5 disclose preparations which are useful in achieving weight loss, treating hyperlipidaemia and the inhibition of Type II diabetes, respectively. These preparations consist largely of L-aspartic acid in combination with creatine, pyruvate and arginine, respectively. These preparations provide no essential amino acids and no source of glucose equivalents is included. Moreover, US 2004/0043013 teaches to consume large amounts of amino acids having drawbacks associated therewith. Creatine can have a deleterious effect on some enzymes of the trans-sulfuration pathways, the relatively expensive pyruvate easily decomposes in liquid formulae and is therefore not an attractive ingredient for use in nutritions, and arginine heavily stimulates the insulin release with the associated problems of putting stress on the pancreas and increasing the risk of developing insulin resistance.

Considering the magnitude of the aforementioned health problems and the low success rate of the solutions that have been disclosed in the prior art, a need exists for nutritional preparations or a dietetic regimen, which is easy to comply with, because of their enjoyable organoleptic properties, which fits in normal day life and feeding/drinking practices, avoids additional stress for the pancreas, maybe even relieves the task of the pancreas, has no undesired side effects and normalizes blood levels of glucose, especially after consumption of food and increases sensitivity to insulin.

SUMMARY OF THE INVENTION

It has been found that high amounts of aspartate equivalents, especially in relative absence of glutamate equivalents, increase the glucose uptake of peripheral cells and improve the reaction of the liver on dietetic glucose consumption. As a result, post-prandial glucose response decreases as well as insulin resistance of the mammal's body, and thus diabetic conditions can be effectively prevented and treated.

According to the invention the mammal's capacity to take up glucose from the blood can advantageously be enhanced using a complete food fortified with aspartate equivalents or a supplement rich in aspartate equivalents that is given simultaneously with or even minutes up to an hour prior to the consumption of a meal comprising glucose. In either case the aspartate-rich nutrition or pharmaceutical preparation has a favourable effect on the blood glucose levels of a person suffering from hyperglycaemia, in particular postprandial and post-surgery hyperglycaemia and/or insulin resistance. It is shown in example 7 that aspartate-enriched foods and foods having a high ratio of aspartate to glutamate make flattening of the glucose levels in blood after the uptake of food comprising glucose occur faster.

Although the use of aspartate- and glutamate-containing sources as for instance soy for combating some of the aforementioned secondary disorders related to hyperglycaemia and insulin resistance is known in the art, this effect has never been attributed to individual amino acids, let alone aspartate and its ratio to glutamate.

Using the invention, a nutritional composition can be given to patients suffering from hyperglycaemia, in particular postprandial and post-surgery hyperglycaemia and/or suffering from insulin resistance, that is enriched in aspartate and/or of which the weight ratio of aspartate to glutamate is chosen to be high and wherein the (essential) amino acid profile can be adapted to meet the requirements of the patients condition and which has acceptable organoleptic properties.

It is now found that a product such as the one taught in U.S. Pat. No. 6,706,697, containing aspartate equivalents in an amount of maximally 10.4 wt %, could be further enriched to achieve optimal success in treating and preventing diabetic conditions.

Hence, with the present knowledge it is for instance possible to combine the favourably high aspartate content of soy with other aspartate-rich proteins, dipeptides and/or aspartate salts to further enhance the glucose uptake and at the same times optimize the organoleptic properties of the product and the amino acid content to the patient's profile. It is also possible to choose a protein from a source other than soy to develop a product for controlling the postprandial glucose response, wherein a high aspartate content, and preferably also a high ratio of aspartate to glutamate, serve as the selection criteria.

Thus, it is an object of the invention to provide a nutritional or a pharmaceutical composition for regulating plasma glucose concentrations and/or increasing insulin sensitivity in a mammal, wherein the nutritional or pharmaceutical composition contains a protein fraction comprising at least 10.8 wt % aspartate equivalents, wherein at least part is provided by an aspartate source containing at least 12.0 wt %, preferably at least 12.3 wt % aspartate equivalents. Preferably, the protein fraction further comprises glutamate equivalents in a weight ratio of aspartate equivalents to glutamate equivalents (asp:glu) between 0.41:1 and 5:1.

Such an aspartate source containing at least 12.0 wt % can be an intact protein, a protein isolate, concentrate or hydrolysate, and/or free aspartate equivalents. If the aspartate source containing at least 12.0 wt % is a protein, a protein isolate, concentrate of hydrolysate, it is preferred that it is present in an amount of 5-100 wt %, more preferably 8-70 wt %, even more preferably 10-60 wt % of the protein fraction. When more than one protein containing at least 12.0 wt % aspartate is present, the above numbers apply to the sum of these proteins. In case the aspartate source is formed from free aspartate equivalents, these are preferably present in an amount of 0.2-9 wt %, more preferably 0.5-6 wt %.

Thus, it is another object of the invention to provide a nutritional composition containing a protein fraction comprising at least 10.8 wt % of aspartate equivalents, based on the weight of the protein fraction. More preferably, the protein fraction further comprises glutamate equivalents, wherein the weight ratio of aspartate equivalents to glutamate equivalents is 0.41:1-5:1, more preferably less than 2:1. It is preferred that the protein fraction comprises a first and a second source of aspartate equivalents, wherein said first source is an intact protein, a protein isolate, concentrate or hydrolysate, and wherein the second source differs from the first source. It can for instance be another protein or protein-derived material or free aspartate equivalents.

It is yet another object of the invention to provide a nutritional or a pharmaceutical composition for regulating plasma glucose concentrations and/or increasing insulin sensitivity in a mammal, wherein the nutritional or pharmaceutical composition comprising at least a protein fraction having a high weight ratio of aspartate equivalents to glutamate equivalents of 0.41:1-5:1, preferably between 0.58:1-2:1.

Preferably the nutritional or pharmaceutical composition comprising the aspartate equivalents is administered simultaneously with or at most 60 minutes prior to a meal comprising glucose equivalents.

It is a further object of the invention to provide a method for regulating plasma glucose concentrations and/or increasing insulin sensitivity in a mammal in need thereof, especially for treating and preventing diabetes and hyperglycaemia, in particular postprandial and post-surgery hyperglycaemia and/or insulin resistance, the method comprising administering the nutritional or pharmaceutical composition of the invention to said mammal.

DESCRIPTION OF THE PREFERRED EMBODIMENTS

Aspartate, Glutamate

The amino acids aspartic acid, asparagine and glutamic acid and glutamine are considered as non-essential amino acids in mammals, as the mammal body has a metabolic capacity to synthesise these amino acids when necessary. The physiological active isomer is the L-form and the endogenous amino acids are typically in equilibrium with their keto-analogues oxaloacetate (for aspartate) and alpha-keto glutarate (for glutamate). Asparagine and glutamine can be hydrolysed in the body to respectively aspartate and glutamate under release of an ammonia group via interaction with the enzymes asparaginase and glutaminase, respectively. Aspartate and glutamate are sometimes considered as neurotoxins.

During the application of standard analysis methods for amino acid contents, asparagine and glutamine are easily hydrolysed, which is why often in amino acid compositions of proteins no separate amount of asparagine is provided but instead an amount for the sum of asparagine and aspartate is given. The same applies to glutamine.

For the purpose of this document, "aspartate equivalents" are defined as components that are able to release L-aspartate in the body, either directly or after digestion, absorption, and metabolic conversion by the liver in situations in which the equivalent has been consumed orally or enterally, for example via tube feeding. Examples of aspartate equivalents are proteins or peptides that comprise L-aspartic acid and/or L-asparagine, free amino acids, either synthesised or extracted from natural materials, salt forms of the free amino acids, for example salts with metal ions like sodium, potassium, zinc, calcium, magnesium or with other compounds like other amino acids, carnitine, taurine, or quaternary ammonium compounds like choline or betaine, the esterified forms of the amino acids, like those compounds which comprise an acyl moiety bound to one of the carboxylic acid moieties, or esters resulting from organic molecules like pyruvic acid, and derivatives of the free amino acids in which an alkyl or acyl group has been attached to the primary nitrogen atom. Thus, aspartate equivalents comprise any compound having the formula $R^1$—NH—CH(COR$^2$)—[CH$_2$]$_n$—CO—OR$^3$ or $R^1$—NH—CH(COR$^2$)—[CH$_2$]$_n$—CO—NHR$^3$, wherein n=1, $R^1$ is H, (substituted) alkyl, or acyl (including C-peptidyl), $R^2$ is OH, OR$^3$, NHR$^3$ or N-peptidyl, and $R^3$ is H, (substituted) alkyl or acyl, as well as the anion and cation salts and zwitterions. The same applies to glutamate equivalents, with the exception that n=2. The peptides are preferably obtained by hydrolysis of intact protein. The keto analogues oxaloacetate and its derivatives are less suitable forms for inclusion in a nutritional product due to technological (processing) and stability problems that may arise.

Dosages are given in grams of L-aspartic acid. Equivalent dosages of alternative components can be calculated by using the same molar amount and correcting for the molecular weight of the alternative component. In the calculations the residues in peptides and proteins are corrected for the lack of a water molecule in the amino acid chain. All equivalents contribute to the total weight in their complete, i.e hydrolysed form, including the water molecule.

"Glutamate equivalents" are defined in a similar way as for the aspartate equivalents. They include proteins or peptides that comprise L-glutamic acid and/or L-glutamine, free glutamate and glutamine amino acids, either synthesised or extracted from natural materials, salt forms of the free amino acids etc. N-Acetyl glutamine and N-acetyl glutamate are also suitable forms. Throughout the description and claims dosages are given in grams of L-glutamine, the equivalents corrected for the lacking water molecule in the case of peptide and protein constituents.

The amounts of aspartate and glutamate equivalents are calculated on the basis of the total nutritional or pharmaceutical composition. In case the composition consists of different portions, the amounts of those equivalents in the different portions are to be added.

Throughout this document, "free aspartate equivalents" or "free glutamate equivalents" are understood to comprise aspartate, asparagine, glutamate and glutamine, their free acid as well as their anionic forms and salts, such as alkali metal salts, alkaline earth metal salts, ammonium salts, substituted ammonium salts and zwitterionic species; the acids are indifferently referred to by their acid name or their anionic names, e.g. aspartic acid or aspartate and glutamic acid or glutamate, respectively. Free aspartate equivalents and free glutamate equivalents also include dipeptides containing at least one molecule of aspartate and glutamate, respectively. The dipeptides serve as a source of aspartate and glutamate, and should not have an independent biological action in the concentration range wherein they are used.

However, it is preferred to use L-aspartic acid or its derivatives instead of L-asparagine or its derivatives in order to prevent production of undesired by-products during processing, in particular when the aspartate equivalents are included in free form, i.e. not as oligo- or polypeptide. Suitable forms of L-aspartic acid are salts with metals like sodium, potassium, calcium, zinc and magnesium or with amino acids like L-lysine and L-histidine.

The amount of aspartate salts is not allowed to exceed 9 wt %, preferably less than 6 wt % of the nutritional preparation, and in particular the amount of each individual aspartate salt should not exceed 4.8 wt % in the case the protein fraction is administered to a patient in a liquid form, in order to avoid electrolyte imbalances. For example the amount of potassium will typically be less than 400, preferably 50-250 and most preferably 100-180 mg per 100 ml. The amount of magnesium will typically be less than 200 mg, preferably 10-120 and more preferably 12-80 mg per 100 ml. Also dipeptides comprising one or more aspartic acid moieties are suitable, though not preferred embodiments. Again an alternative source is plant extracts like extracts from sugar cane, especially those that are rich in aspartate and betaine or extracts from potato. By at least partial hydrolysis the aspartate fraction becomes more rapidly available to the patient.

Because of its importance in combating the aforementioned disorders, the amount of aspartate equivalents can be further increased, but the protein fraction should contain no more than 95 wt %. The protein fraction preferably comprises at least 10.8 wt % of aspartate, preferably 11.0-70 wt %, more preferably 11.5-50 wt %, even more preferably 11.8-45 wt %, even more preferably 12.0-40 wt % and most preferably 12.5-36 wt %, in particular 12.8-30 wt % more in particular less than 25 wt % of aspartate equivalents, based on the weight of the protein fraction. A protein fraction containing more than 13.0 wt %, or even more than 14.0 wt % of aspartate equivalents is particularly preferred.

A protein fraction according to the invention preferably comprises an aspartate fraction that is rapidly digested and absorbed and therefore available in the body. This can be achieved by including at least part of the aspartate equivalents in a form that passes the stomach rapidly, and does not put high demands on the activity of digestive enzymes like pepsin, trypsin and chymotrypsin. In one embodiment it is thus preferred that at least a part, preferably at least 0.2 wt %, more preferably at least 0.5 wt %, even more preferably at least 0.7 wt % and most preferably at least 1.0 wt %, in particular at least 1.5 wt % of the aspartate equivalents are synthetic or isolated amino acids and/or salts or esters thereof, and/or dipeptides containing at least one molecule of aspartate equivalents.

Further, the protein fraction of the invention preferably comprises 0.2-30 wt % of glutamate equivalents, preferably in an amount of 2.0-25.0 wt %, more preferably 4.0-22.0 wt %, even more preferably 5.0-22.0 wt % and most preferably 8.0-21.0 wt %, in particular 10.0-20.5 wt %, based on the weight of the protein fraction. Sometimes a protein fraction containing 12.0-18 wt % of glutamate equivalents is preferred.

A relatively high weight ratio of aspartate equivalents (asp) to glutamate equivalents (glu) has a beneficial effect according to the invention. Especially in products for young infants and babies, the weight ratio of aspartate equivalents to glutamate equivalents is of great importance. Therefore, the protein fraction has a weight ratio of asp:glu of between 0.41:1 and 5:1, preferably between 0.45:1 and 4:1, more preferably between 0.50:1 and 3:1, in particular between 0.53:1 and 2:1. In another embodiment, especially for those cases where the product consists largely of soy-based proteins, preferably more than 50 wt %, more preferably more than 60 wt %, most preferably more than 70 wt % of the protein fraction, an even higher asp:glu weight ratio is preferred. Then the protein fraction preferably has a weight ratio of aspartate equivalents to glutamate equivalents that is preferably between 0:58:1 and 2:1, preferably in the range of 0.59:1-1.8:1, more preferably 0.60:1-1.6:1, even more preferably 0.62-1.4:1 and most preferably in the range of 0.70:1-1.2:1.

Obviously better results are obtained when the extent to which the criteria as set to the product according the invention are met becomes larger. In particular this is true for the total amino acid composition and the inclusion of a source of aspartate equivalents that is more rapidly available to the consumer of the product compared to the glucose fraction.

Protein Fraction; Amino Acid Profile

The "protein fraction", as used throughout the description and claims, is defined to be the sum of all proteins, peptides and amino acids in the product, and with protein is also understood protein isolate, concentrate and/or hydrolysate. The protein fraction is effective when it meets the following criteria:

In addition to the conditions on the amounts of aspartate and glutamate equivalents, the amount of essential amino acids in the protein fraction, such as methionine, branched chain amino acids valine, leucine and isoleucine, and further lysine, tyrosine, phenyl-alanine, histidine, threonine and tryptophan, that will become available to the organism of the mammal after digestion of the protein fraction should provide sufficient amounts to ensure anabolism and proper functioning of the body.

In particular, it has been found that the amounts of L-methionine and L-lysine but also L-leucine are critical. Except for the case wherein the patient suffers from tumour growth, the amount of L-methionine is preferably 1.5-4 wt % and more preferably 1.7-3.3 Wt % of the protein fraction. Then, the sum of the amount of L-methionine and L-cysteine in the protein fraction is preferably above 2.7 wt %, more preferably above 2.9 wt % and most preferably 3.5-8 wt % of the protein fraction. In the case that a patient suffering from net insulin resistance and/or hyperglycaemia also suffers from tumour growth, it is preferred that the protein fraction is not supplemented with L-methionine.

Patients suffering from propionic academia do not tolerate high amounts of isoleucine, valine, methionine and threonine that catabolise to propionic acid in the diet. With the product of the invention the amount that is tolerated can be increased. The total amount of these amino acids in the protein fraction is therefore above 10, preferably 12-30, more preferably 16-26 wt % of the protein fraction. The same criterion holds for products that are used by persons that suffer from methylmalonic academia.

The amount of L-lysine is preferably 5.5-15, more preferably 6.6-12 and most preferably 7.1-11 wt % of the protein fraction. However, if it is to be administered to persons suffering from glutaric academia the amounts of lysine must be below 7 wt %, preferably 5.5-6.9 wt % of the protein fraction. In that case the tryptophan levels should be below 1.7, preferably 1.3-1.6 wt % of the protein fraction.

In order to avoid a large release of insulin upon administration, the concentrations of arginine, glycine and phenylalanine in the protein fraction must be relatively low.

The amount of arginine is preferably less than 7.9 wt %, more preferably less than 7.8 wt %, even more preferably less than 7.0 wt % and most preferably less than 6.0 wt % of the protein fraction. The ratio of L-arginine to L-lysine in the product will typically be 0.4:1-1.43:1, preferably 0.5:1-1.40:1, and especially in products to be administered to young infants the ratio is preferably 1:1-1.40:1. The ratio of aspartate equivalents to L-arginine in the product is preferably higher than 1.4, more preferably 1.5-5, most preferably 1.6-3.0 to achieve maximum effect and a balanced amino acid profile.

The amount of L-glycine is preferably higher than 3.5, preferably between 3.6 and 4.5 wt % and more preferably less than 4.2 wt % of the protein fraction. The weight ratio of Asp/Gly is preferably in the range 2.8:1-100:1 and that of Asp/Phe in the range 2.4:1-100:1. In particular the amount of L-serine must exceed the amount of L-glycine by at least a factor 1.5. Preferably the ratio L-serine/L-glycine is larger than 2.0:1 and more preferably at least 2.3:1. This can be achieved by adding proteins that comprise a lot of L-serine relative to L-glycine and/or by adding synthetic L-serine or dipeptides which comprise L-serine.

The amount of L-phenylalanine is preferably lower than 5.6 wt % and more preferably less than 5.3 wt % of the protein fraction. Aspartame is an unsuitable source of aspartate, also because of its extreme sweetness.

The amount of leucine in the protein fraction of the products according the invention is 7.7-13 wt %. Persons that suffer from isovaleric academia desire levels of leucine below 10 wt %, preferably below 9.0 wt %. For persons that have underdeveloped and/or imparted metabolic functions like young infants, pre-term infants and persons having severely imparted liver function, the weight ratio of aspartate relative to leucine is preferably in the range of 0.85:1-1.5:1, more preferably 0.88:1-1.4:1, even more preferably 0.9:1-1.1:1 and most preferably a value in the range of 0.95:1-1.04:1. In order to keep the amount of aspartate and leucine in balance it is recommended to include part of the amount of leucine as alpha-keto-isocaproate. This component is an excellent counterion for components like amino acids or ornithine or betaine in terms of affectivity and taste.

It is especially preferred to use a protein fraction satisfying the level of aspartate equivalents according to the invention in the preparation of a product for treatment of metabolic disturbances, wherein the protein fraction further comprises one of: a) 7.7-19 wt % of the sum of all branched chain amino acids; b) 7.7-9.0 wt % leucine and 3.6-4.5 wt % glycine; c) 16-26 wt % of the sum of isoleucine, methionine, valine and threonine; and d) 5.5-6.9 wt % lysine and 1.3-1.6 wt % tryptophan, wherein the numbers are based on the weight of the protein fraction.

The amount of L-histidine is preferably 2.3-4 and more preferably 2.5-3.2 Wt % of the protein fraction. The amount of alanine in the protein fraction will typically be 4.8-8, preferably 5.1-7.5 and more preferably 5.3-7.0 wt %.

Organic molecules comprising a guanidino group can be beneficially included in the product. However, it is recommended not to include free arginine or its equivalents like salts or small peptides that comprise L-arginine. Instead, low amounts of guanidino-acetate or 3-guanidino-propionate can be included, e.g. in amounts below 2 g per daily dose and preferably in amounts of 0.1-1 g per daily dose. In a liquid product 3-guanidino-propionate is an excellent source and its concentration will typically be 0.005-0.05 wt %. It is therefore preferred to include no or only relatively low amounts of creatine such that the weight ratio of creatine/aspartate equivalents in the protein fraction is less than 0.2:1, preferably even less than 0.1:1, more preferably even less than 0.5:1 to avoid potential deleterious effect of creatine on some enzymes of the trans-sulphuration pathways. This is important that the product has to act on some secondary side effects of hyperglycaemia and/or insulin resistance like some vascular disorders like hypertension and erectile dysfunction.

As a source of methionine synthetic L-methionine, salts thereof, e.g. those with alkali metals, calcium, magnesium, zinc or organic acids like citric acid or malic acid or amino acids like aspartic acid can be used. It is preferred to use a form that tastes better than the synthetic L-methionine. Suitable forms are acylated methionine, e.g. the N-acetyl methionine as has been described in EP 0758852 and U.S. Pat. No. 1,560,000, and the methionine analogs as disclosed in U.S. Pat. No. 5,430,064. A small amount of the methionine may suitably be added as zinc methioninate complex. In order to avoid that the total dose of zinc exceeds 100 mg per day the amount of zinc methioninate should be below 1 wt % of the protein fraction.

Embodiments

In one embodiment of the invention the nutritional or pharmaceutical preparation comprises a protein fraction of a first aspartate-rich source, i.e. a protein, a protein concentrate, isolate or hydrolysate or even free aspartate equivalents, wherein the first aspartate-rich source contains more than 12.0 wt %, preferably at least 12.3 wt % aspartate equivalents, and an aspartate-rich second source different form the first source. The second source of aspartate equivalents can be another protein, preferably comprising at least 7.8 wt %, more preferably at least 8.0 wt %, even more preferably at least 9.0 wt %, more preferably at least 10.0 wt %, even more preferably at least 10.5 wt % aspartate equivalents. The choice of free aspartate equivalents as a first source is especially favoured in the case where a fast absorption of aspartate from the diet in the blood is required. Other preferred choices of the first aspartate-rich source are lactalbumine-enriched whey and potato protein.

It is preferred that the preparation comprises at least two proteins. In order to meet all these nutritional criteria at the same time it appears that a combination of a protein from plant origin and one of animal origin is most suitable. In addition, it appears that in this way the resulting taste of the protein source is much better than when using proteins that only consist of protein from plant origin. The use of the combination of a protein of plant origin and one of animal origin also allows rapid availability of the aspartate equivalents, especially in the case where at least one of the proteins is partially hydrolysed. If a protein is partially hydrolyzed, it is preferred that it is the protein of plant origin, especially in case of a liquid formulation, whereas the protein of animal origin can be non-hydrolysed or only slightly hydrolysed, in order to increase solubility of the protein and to obtain a liquid that is stable also during processing, in particular during heating. The degree of hydrolysis is then preferably 5-70%, more preferably 8-60%, most preferably 11-50%. The weight ratio between the protein from plant origin and the protein of animal origin is preferably between 4:1 and 1:4, more preferably between 3:1 and 1:3, most preferably between 2:1 and 1:2.

Table 1 provides some comparable data which clarify the differences between the protein composition according to the invention and individual proteins known in the art.

TABLE 1

Amino acid composition of common ingredients (wt % of protein fraction)

|  | soy | whey[#] | EWP[#] | milk[#] | casein | pea | potato | invention | invention (optional) |
|---|---|---|---|---|---|---|---|---|---|
| aspartate eq. | 11.8 | 10.4 | 9.9 | 8.0 | 7.8 | 8.4-11[$] | 21 |  | 10.5-95 |
| glutamate eq. | 20.5 | 18.2 | 15.3 | 22.7 | 25.0 | 15.1 | 22.5 |  | 0.2-30 |
| wt ratio asp/glu | 0.57 | 0.57 | 0.64 | 0.35 | 0.31 | 0.55-0.73 | 0.93 | 0.41-5 |  |
| L-lysine | 5.6 | 9.2 | 6.5 | 8.8 | 10.2 | 9.3 | 6.4 |  | 5.5-15 |
| L-methionine | 1.6 | 1.9 | 4.3 | 2.7 | 3.3 | 1.5 | 1.5 |  | 1.5-4 |
| L-arginine | 7.8 | 3.0 | 6.2 | 3.6 | 4.0 | 16 | 5.9 |  | 1.0-7.9 |
| L-glycine | 4.4 | 1.9 | 4.7 | 2.1 | 2.0 | 2.6 | 5.9 |  | 1.0-4.5 |
| L-phenylalanine | 5.5 | 3.2 | 6.9 | 5.1 | 5.6 | 6.1 | 4.9 |  | 3.2-5.6 |
| L-histidine | 2.5 | 1.6 | 2.3 | 3.0 | 3.2 | 3.4 | 2.0 |  | 2.3-4 |
| L-leucine | 7.7 | 10.4 | 8.4 | 10.2 | 10.5 | 7.5 | 5.7 |  | 7.7-13 |

[#]whey is the bulk desalted whey protein from cow's milk;
EWP = egg white protein;
milk stands for cow's milk;
[$]aspartate levels depend on the type of species (see e.g. Souci, Fachmann and Kraut in Food composition and Nutritional Tables, 6[th] ed, Stuttgart, 2000), and the protein isolation method.

When the optimal amino acid composition as disclosed in Table 1 is applied in products for persons that suffer from an inherited metabolic disorder, it is important that the remainder of the amino acids present in the product complies with the specific nutritional demands of this particular type of patient. For example, if the product is used by a person that suffers from Maple Syrup Urine Disease, the product should comprise low amounts of branched chain amino acids e.g. less than 20 wt % of the protein, e.g. 7.7-19 wt %.

Several raw materials can be effectively used in the protein fraction according to the invention. Whey, soy, lupine, potato, meat, liver, fish, white bean, lima bean, lentil, pigeon pea, some other pea species such as yellow Canadian pea, and black gram comprise relatively high levels of proteins that are relatively rich in aspartate equivalents compared to glutamate equivalents. Specific whey fractions of the milk of all mammals, in particular of cow, buffalo, horse, goat, sheep and camel, can be used as long as they meet the above criteria. For practical reasons and because of its beneficial amino acid composition, whey from cow's milk is particularly suitable as starting material in most cases, for example sweet whey that results after cheese manufacture or acid whey. The latter is a very suitable source due to the absence of glycomacropeptide.

Raw whey from cow's milk comprises numerous proteins like beta-lactoglobulin, immunoglobulins, lactoferrin, bovine serum albumin, alpha-lactalbumin and several others. Pure alpha-lactalbumin but also whey fractions that comprise more than 20% of the sum of these proteins and preferably between 30-90 wt % and most preferably 33-70 wt % can beneficially be used for the purpose of the invention. Very suitable whey proteins are α-lactalbumin-enriched whey proteins having a content of aspartate equivalents of at least 12 wt % and an asp:glu ratio of at least 0.58, as exemplified in Table 2.

TABLE 2

Examples of the amino acid composition of two suitable whey fractions of cow's milk for use in the products according the invention

|  | LP[$] | a-whey[#] |
|---|---|---|
| aspartate equivalents | 12.3 | 13-13.5 |
| glutamate equivalents | 21.2 | 16.2 |
| weight ratio asp:glu | 0.58 | 0.80-0.83 |
| L-lysine | 10.7 | 9-10.1 |
| L-methionine | 2.4 | 1.6 |
| L-arginine | 3.0 | 1.8 |
| L-glycine | 2.2 | 2.1 |
| L-phenylalanine | 3.7 | 3.3-3.8 |
| L-histidine | 1.6 | 2.4 |
| L-leucine | 11.8 | 12.1 |

[#]a-whey is a specific whey fraction isolated from cow's milk and that is enriched in alpha lactalbumin;
[$]LP stands for a commercially available whey fraction that is enriched in alpha-lactalbumin.

Potato protein is a very suitable form of rapidly available aspartate and hydrolysis as such is not required when it is included in dry products. However in liquid products it should be hydrolysed in order to increase their solubility. The same applies to proteins which are readily digested, like meat products in non-fat nutritional products. Meat or liver proteins such as those having an aspartate equivalent content between 8.5 and 11 wt. % and an asp:glu ratio between 0.55 and 0.9 are very suitable.

It is preferred that the preparation according to the invention comprises a protein from animal origin selected from meat, milk whey or liver, and a second protein from plants selected from soy, lupin, pea, in particular pigeon pea, beans, in particular white bean, lima bean, lentil or black gram, and potato. It is especially preferred that the protein fraction comprises a soy hydrolysate or concentrate, or a dairy product. With dairy product is understood a protein fraction that comprises at least 80 wt % of dairy proteins such as proteins isolated from milk of cow, buffalo, camel, horse, goat, and sheep. The two main protein constituents of milk are whey (20 wt %) and casein (80 wt %). Such a soy protein hydrolysate or concentrate or a dairy product with an outbalanced essential amino acid profile can be enriched with aspartate equivalents using small amounts of an aspartate-rich protein, e.g. pea protein, potato protein or alpha-lactalbumin. The amount of such a second protein is preferably lower than 70 wt %, more preferably lower than 40 wt %, even more preferably lower than 30 wt % and most preferably lower than 20 wt % of the protein fraction.

Several of the raw ingredients that comprise a protein fraction that satisfy the requirements of the invention are rich in anti-nutritional factors like haemaglutinins, phytic acid, tannins, flavonoids and protease inhibitors. The amount of these components in the protein fractions should preferably be very low, which can be achieved by applying suitable isolation practices either alone or in combination with heat treatment (so called "toasting") as is described in the art. In order to ensure that a rapidly available aspartate source is included in the product it is important that the amount of protease inhibitors are low, in particular when intact proteins or slightly hydrolysed proteins have been included as aspartate equivalents. The amount of protease inhibitors can for example be quantified as remaining Trypsin Inhibitor Activity (TIA) or as concentration of Bowman-Birk inhibitors by using methods known in the art. Typical levels are below 0.12 g, preferably below 0.06 g, more preferably below 0.02 g and most preferably below 0.007 g per kg of the protein fraction. In particular the level of inhibitors of chymotrypsine should be below 0.01, preferably below 0.004 per kg of the protein fraction. The amount of adequately treated soy protein isolates are 1-6 TIA per g of the protein fraction.

By mixing several of the protein fractions of the ingredients as mentioned an amino acid profile can be obtained which fulfils the criteria as set according to the invention for complete nutrition. In an embodiment of the invention mixtures of soy protein and synthetic amino acids or soy protein with specific whey proteins, in particular whey proteins that are enriched in alpha-lactalbumin are preferred.

It is preferred that at least one of the proteins is hydrolysed in case that no free L-aspartic acid or salts thereof are included in the product, though an important part of the total protein should remain intact for taste considerations. Typically 30-95 wt % of the protein fraction is intact, preferably 40-92, more preferably 50-89 wt %, even more preferably at least 60 wt % and especially at least 70 wt % of the protein fraction. As described above, it is preferably that the vegetable protein source is hydrolysed rather than the protein of animal origin, in particular because of organoleptic and product stability reasons, e.g. during heat treatment and/or shelf life. For example a protein fraction that is prepared by mixing 95 wt % soy protein isolate, and 2 wt % L-aspartate and 1 wt % L-lysine and 1 wt % L-methionine would meet the criteria as set.

In some embodiments it is preferred to use a large fraction of soy protein isolate or hydrolysate. It is however preferred to use less than 92 wt % of soy protein isolate, which provides about 10 wt % of aspartate equivalents, preferably less than 90 wt % of soy protein isolate and even more preferably even less than 85 wt % of soy protein isolate. The protein fraction is then fortified to the required level of aspartate equivalents using non-soy protein containing at least 12.0 wt % of aspartate equivalents or free aspartate equivalents that are rapidly digestible.

Examples of combinations of proteins satisfying the criteria of the invention are a mixture of 83 wt % hydrolysed soy protein concentrate, 15 wt % hydrolysed alpha-lactalbumin enriched whey protein (as provided by Aria) and 0.5 wt % L-methionine, 0.5 wt % L-histidine and 1 wt % L-serine, or a mixture of 40 wt % soy, 50 wt % meat protein and 10 wt % potato protein, or a mixture of 50 wt % hydrolysed soy protein isolate and 48 wt % cow's milk whey fraction, 0.5 wt % N-acetylmethionine, 0.5 wt % L-histidine and 1 wt % serine.

Where it is preferred to prepare a composition on dairy basis, especially in the treatment of young infants suffering from or at risk of developing hyperglycaemia, insulin resistance or child obesity or diabetes the amount of dairy or milk proteins is at least 50 wt % of the protein fraction, preferably at least 60 wt %, more preferably at least 70 wt % and most preferably at least 80 wt % of the protein fraction. Such a composition is to be fortified with an aspartate-rich source to make the composition satisfy the criteria of at least an asp:glu weight ratio according to the invention.

Though many components can serve as a metabolic precursor of aspartate after digestion in the gastrointestinal tract several of these components are preferred. Intact proteins from several sources as well as their hydrolysates are recommended. It is therefore preferred that the protein fraction comprises peptides, intact proteins and/or hydrolysates thereof.

Glutamate equivalents are abundantly present in the proteins as selected to meet the requirements of the amino acids. It is however only useful to include N-acetyl glutamine as long as the aforementioned requirements for the total protein composition are met and the total amount of N-acetyl glutamine does not exceed 50 wt % of the amount of glutamate equivalents, preferably is in the range of 2-40 and more preferably 5-25 weight percent of the amount of glutamate equivalents, based on the weight of the protein fraction. The latter is important to avoid homeostasis problems with nitrogen balance. However, as this does not play a dominant role in cases of hyperammonemia, the restriction on the fraction of N-acetyl glutamine does not apply when hyperammonemia is diagnosed in a patient.

It is preferred that if the proteins are used in combination with carbohydrates in the total diet, the amount of protein provided must be less than the amount of digestible carbohydrate. Typical amounts of protein in products that are meant to be used as complete nutrition will comprise 10-30, preferably 15-25 and more preferably 18-22 energy percent, in particular about 20 energy percent.

The protein fraction will preferably comprise no or low amounts of caseins or its hydrolysates, because it is a poor source of aspartate equivalents and comprises too much glutamate equivalents for the purpose of the invention. The amount must be less than 40 wt %, preferably less than 25 wt % of the protein fraction, more preferably less than 10 wt % and most preferably less than 5 wt %.

In order to estimate the daily amount of the ingredients of the nutritional composition that is to be administered to achieve a beneficial effect on the levels of glucose, the protein weight percentages throughout the text can be converted to a daily dosage using the following calculation, thereby assuming that the total energy supply for a patient is about 2000 kcal/day for a body weight of 70 kg: A typical nutritional composition of the invention contains about 20 energy percent of a protein fraction, and thus the total amount of protein fraction administered to a patient per day is about 400 kcal, or in weight terms, about 100 g protein fraction. Therefore, a daily dose can be calculated on the basis on a protein consumption of 100 g per day and, by way of example, a required asparate content of e.g. 12 wt. % of the protein fraction corresponds to a daily dosage of 12 g aspartate. If desired, these amounts can be adapted to the actual body weight by multiplying the required amount by B/70, wherein B is the bodyweight in kilograms. For calculating the optimal doses for an infant, an energy supply of 560 kcal and a protein content of 10 energy percent can be assumed, leading to a protein consumption of 56 kcal or 14 grams, and this results in multiplying the required aspartate content by a factor of 0.14 (1/7). For example, a required aspartate content of 12 wt. % corresponds to a daily dosage of 12×0.14=1.68 g. If desired, these amounts can be adapted to the body weight by multiplying by B/2, 2 kg being the weight of an infant used as a starting point for these calculations.

Carbohydrate Fraction

It is preferred to use the protein fraction in combination with at least a carbohydrate fraction. The fraction of carbohydrates in the diet must be relatively slowly digested in the gastrointestinal tract of the mammal compared to the protein fraction that comprises the aspartate equivalents. Best results are obtained using a product demonstrating a glycemic index below 70 and preferably below 55. This can advantageously be achieved using a carbohydrate fraction exhibiting a glycemic index below 90, preferably between 15 and 70, more preferably between 25 and 55. The glycemic index compares the immediate effect of the carbohydrate fraction on plasma glucose levels compared to glucose, which is given the value 100. The method to determine glycemic index including values for several carbohydrates is described in the art.

Suitable sources of digestible carbohydrates can be any food grade carbohydrate extract from tubers or cereals like barley, oats, potato, corn, wheat, rye, triticale, millet, sorghum, amaranth, rice, sugar cane, sugar beet, cassaye, tapioca, etc.

The digestible carbohydrate fraction can comprise two types of carbohydrates: (i) the glucose equivalents, which are understood to be glucose polymers, glucose oligomers, disaccharides that comprise glucose, and glucose itself, and (ii) carbohydrates that comprise predominantly monosaccharide units that differ from glucose. The latter category is typically difficult to digest in the gastrointestinal tract of man. However, often the monosaccharides themselves and several disaccharides are relatively easy to absorb and to digest.

Preferably the aspartate equivalents are administered in an amount corresponding with a weight ratio of aspartate equivalents to glucose equivalents of 0.037:1-2:1, more preferably of 0.045:1-1.8:1, even more preferably of 0.050:1-1.5:1 and most preferably 0.060:1-1:1. With the glucose equivalents is understood all glucose that is administered in one or more portions of the nutritional or pharmaceutical preparation, but also the equivalents that are comprised in the meal that the person consumes within 60 minutes after administration of the aspartate-rich preparation. For the purpose of calculating the aspartate to glucose ratio, any glucose occurring in α-glucans, glucose itself, sucrose and lactose is included whether or not the glucan is readily or difficulty absorbable or digestible.

Sources of digestible carbohydrates can be treated in such a way that the carbohydrates are difficult to approach by the digestive enzymes. Examples are resistant starches. The carbohydrates can also comprise glucose moieties which are attached to each other via beta-1,6- or alpha-1,1 glycosidic bonds which are difficult to hydrolyse by the normal digestive enzymes. Examples of this type of carbohydrates have been described in the art, for example in WO 2004/023891, modified starches and pullulan as described in WO 03/105605. Also the use of highly branched carbohydrates like high-amylopectin carbohydrates delays digestion and can suitably be included, like those starches that comprise more than 75 wt % amylopectin, preferably when they are lightly hydrolysed. Suitable sources have been genetically modified or obtained via selection of plants like potato, tapioca, corn, cassaya or cereals like sorghum, wheat, rye, triticale, barley, oats or millet. Other sources that can partially be included in the formula are those maltodextrins which comprise high amounts of polymers having more than 9 monosaccharide units. By using a small degree of hydrolysis of the intact starches a suitable source of glucose is obtained. Digestion can further be delayed by using additives during hydrolysis of the starch, which leaves the structure of the membrane of the starch granule more intact, like has been disclosed in U.S. Pat. No. 6,720,312.

About 40-100 wt % of the carbohydrate fraction must be formed of glucose equivalents. Preferably this amount is 45-90, more preferably 49-80 and most preferably 52-75 wt %. Useful glucose equivalents are for example glucose polymers having a chain length of more than 9 units, that for example occur in maltodextrins DE 2-31, and some glucose syrups. Other useful glucose oligomers are those in which glucose occurs together with other monosaccharides like galactose, fructose, xylose, arabinose, mannose, fucose, rhamnose, sialic acid or hexuronic acids, which are included in an amount of 1-60 wt % of the glucose equivalents. For young infants it is preferred to include glucose equivalents in which one of fucose, rhamnose, sialic acid or hexuronic acids are included. Suitable ingredients can be extracted from milk, in particular goat's milk. Examples have been given in EP0957692. For the latter group of users these are preferably used in an amount of 1-40 wt % of the glucose equivalents.

Glucose polysaccharides that comprise more than 80 wt % glucose are particularly useful for inclusion in dry products. Examples are starch types which demonstrate delayed digestion due to chemical or physical modification of the granule or the starch molecules. For the purpose of the invention, resistant starch can be determined by applying the method of Englyst an Cummings, Adv. Exp. Med. Biol. 270, 205-225 (1990). Resistant starch may preferably be present at a level of 10-80, preferably 15-60, more preferably 20-40% by weight of the non-digestible carbohydrate (fiber) fraction.

Other examples of suitable glucose equivalents are oligosaccharides that comprise for more than 50 wt % glucose and that have a chain length of 3-9. The amount of these oligoglucosides should be less than 50, preferably less than 40, and most preferably less than 30% of the weight of the digestible carbohydrates. The amount of pure glucose must be low due to its contribution of osmotic value and its sweetness. Preferably the amount is below 10 wt % of the carbohydrate fraction, more preferably 1-8 wt %.

Of the category of disaccharides that comprise a glucose moiety, in particular sucrose and lactose, it is preferred not to include sucrose at more than 5 wt % of the digestible carbohydrate fraction because of its sweetness and contribution to the osmotic pressure of the product. Despite the fact that the latter property also applies to lactose, it is preferred to include lactose in the product unless a clear intolerance for lactose exists. The latter also holds for nutritional products that comprise a protein fraction having more than 5 wt % protein that originates from plants, like soy, lupine, pea, potato, etc.

The category of monosaccharides other than glucose can also be included in the product, though at little amounts, because they contribute heavily to osmotic value and to some extent to sweetness and may cause abdominal complaints. Examples of monosaccharides are arabinose, arabitol, mannose, ribose, galactose, rhamnose, xylulose, xylitol and fructose. The amount of hepta-carbon saccharides like sedo-heptulose should be less than 10 and preferably less than 5% of the weight amount of monosaccharides. The amount of the sum of all monosaccharides that are different to glucose must be less than the amount of glucose equivalents in the product and preferably less than 0.8 times the amount of glucose equivalents. In other words these amounts will therefore be 1-40, preferably 2-30 and more preferably be 3-20 wt % of the fraction of digestible carbohydrates.

When fructose is included it is preferred to include it in relatively limited amounts. The amount of fructose must be in the range of 0.1-20 wt % of the digestible carbohydrates in order to keep the plasma level below 150 and preferably below 120 microM. This is achieved preferably by inclusion of 0.2-15 wt %, preferably 0.3-10 wt %, more preferably 0.4-5 wt %, and most preferably 0.5-4 wt % of fructose, based on the weight of the carbohydrate fraction. In this way less than 2 g fructose is consumed per meal and preferably less than 1 g. On the other hand at the same time more than 2 g glucose units are consumed and preferably more than 10 g per meal. The weight ratio glucose/fructose is above 2:1 and preferably 5:1-100:1 and most preferably 10:1 to 50:1.

Apart from glucose and fructose also D-galactose is a preferred monosaccharide. When the latter is included the amount must be 1-20 and preferably 2-10% of the weight of the monosaccharides in the products.

Digestible carbohydrates are defined to be those carbohydrates that will be hydrolysed for more than 80% after exposure to the digestive enzymes as occur in the gastrointestinal tract and will subsequently be absorbed by the gut. The total amount of digestible carbohydrates must be 10-70 energy percent, preferably 20-65, more preferably 30-60 and most preferably 34-55 en % of the total nutritional composition.

Using the aforementioned calculations on the conversion of the amount of proteins in the nutrition to the daily doses thereof, thereby assuming a total energy supply for a patient of about 2000 kcal/day, a bodyweight of 70 kg and a preferred 40 en % of digestible carbohydrates, the total amount of digestible carbohydrates administered to a patient is about 800 kcal/day, or in weight terms about 200 g digestible carbohydrates per day. It is easy for a skilled person to determine the daily dosage for a particular patient by converting these numbers to the appropriate body weight.

Digestion of carbohydrates can also be retarded by co-inclusion of components which decrease rate of digestion such as polyphenolic compounds or dietary fibres. It is preferred not to include polyphenols in the product, in order to avoid undesired interactions with proteins like those that occur in the product or with the enzymes that act in the digestive system. In particular the amount of flavonoids and tannins, in particular the isoflavones, as may occur in commercially available protein fractions of soy or other plants, should remain below 200 mg, preferably below 100 mg and more preferably below 50 mg per daily dose. Per liter product the concentrations will therefore be less than 100 mg, preferably less than 50 and more preferably less than 25 mg polyphenol per liter product. In order to achieve this, the protein fractions isolated from vegetable material that is rich in polyphenol content will typically be treated for example by washing with an organic solvent like ethanol.

It is preferred that the carbohydrate fraction contains dietary fibres. Dietary fibres can be anionic polysaccharides or other poly- or oligosaccharides like for example those originating from gums like xanthan gum, Arabic gum, Konjac gum, gellan gum, tara gum and guar gum, from pectins, inulin, alginates, carragheenans, like the kappa or iota variants, sulphated dextrans, beta-glucans especially those derived from yeasts like *Saccharomyces cerevisiae*, fibers from pea, like pea hull, barley, wheat, oats or rice, or hydrolysed forms of these dietary fibers. The fibers should have a low intrinsic viscosity in order to allow inclusion in effective amounts in a tube feeding. The viscosity of the final liquid form of the product needs to be 1-30 cP as measured at 20° C. and at 100 per second. The use of oligosaccharides obtained by hydrolysis of the naturally occurring fibers or selection of specific isolates of the naturally occurring fibers is recommended. Effective amounts are typically 1-30, preferably 1.5-20 and more preferably 1.8-15 g dietary fiber per daily dose for an adult. In liquid products the amounts are typically 0.05-4.0, preferably 0.075-2.5 and more preferably 0.09-1.5, especially 0.1-1.0 wt % of the carbohydrate fraction. The amount for infants can be calculated by correcting via body weight. Surprisingly it has been found that especially wheat bran or low-methylated pectins are especially effective dietary fibres. As described above, resistant starch is an important part of the fiber composition.

Lipid Fraction

If present, the lipid fraction should be predominantly digestible and in particular not impart the rate of digestion and absorption of the aspartate fraction compared to the glucose equivalents.

The fatty acids within the lipid fraction predominantly have a chain length of 18 carbon atoms or more, the so-called long chain fatty acids. In particular more than 50 wt %, preferably 60-90 wt % and more preferably 65-80 wt % of the fatty acids are LC fatty acids, i.e. having a chain length of 18 or higher. The amount of unsaturated fatty acids that have a trans configuration is less than 0.8 wt %, preferably <0.5 wt % and more preferably 0-0.3 wt % of the sum of the fatty acids. The amount of medium chain triglycerides can be 0-20 wt % of the sum of the fatty acids and preferably 0-10 wt %. The amount of arachidonic acid is relatively small: 0-5% and preferably 0-3% of the weight of the fatty acids. This will make the weight ratio of zinc to arachidonic acid larger than 0.5 and preferably more than 0.8. The total amount of fatty acids in the product can be determined by extraction of the lipid fraction and determination of the fatty acids in the lipid fraction by applying AOAC method 992.25.

Oleic acid is an important constituent in the lipid fraction. The amount is in the range of 30-60 wt % of the fatty acids. The amount of $\omega$-3 long-chain polyunsaturated fatty acids LC-PUFA's, like eicosapentaenoic acid (EPA) and docosahexaenoic acid (DHA) is relatively high. The total amount of $\omega$-3 LC-PUFA's is 0.5-20 wt % and preferably 1-15 wt % of the fatty acids. The sum of EPA and DHA is preferably 0.5-10 wt %, more preferably 1-10 wt % of the fatty acids. The amount of saturated fatty acids should preferably be less than 10 wt % of the weight of the sum of the fatty acids.

The lipid fraction includes essential long chain fatty acids like linoleic acid and alpha-linolenic acid as recommended by food authorities, in amounts of 0.8-1.5 times, preferably 1-1.2 times the required daily dose. The amount of $\omega$-6 LC-PUFA's, in the lipid fraction is relatively small. The amount of linoleic acid must be 5-35, preferably 6-25, more preferably 7-20 wt % of the sum of all fatty acids.

It is preferred to include the fatty acids to an important extent as phospholipids. The amount of phospholipids is 6-50, preferably 7-30 and most preferably 8-25 wt % of the lipid fraction.

Important sources of fatty acids include structured lipids and natural oils like marine oils like fish oil and krill extract, rice bran oil and high oleic vegetable oils, like olive oil and high oleic safflower oil, peanut oil and canola oil or high oleic sunflower oil extract like trisun-80.

The total amount of lipids in complete formulae for adults and adolescents is therefore more than 30, preferably 32-60 and most preferably 35-45 energy percent of the nutritional composition. In case the product is meant to be used for infants, especially premature infants, the lipids provide 30-42, preferably 31-40, more preferably 31-39 percent of the total energy in the formula. This is in particular important for infants that have underdeveloped metabolic systems like preterm babies and for infants that are at risk for developing insulin resistance or early obesity or diabetes, as for example becomes apparent from prevalence of these disorders or diseases in relatives, or becomes apparent in infants with unbalanced immune systems. Examples of the latter group of infants are those infants that have a low activity of T Sells of type 1 in relation to the activity of T cells of type 2. This can be determined by measuring the amount of cytokines that are specific for T cells type 1 (like interferon gamma) and for T cells of type 2 (like interleukin-4 or 5) and comparing their weight amounts. Infants that demonstrate abnormal (too low) values of the weight ratio Interferon-gamma to (IL-4+IL-5), for example a ratio below 1 are defined to have an unbalanced immune system and may also lead to allergic or atopic reactions.

Product

The products according the invention can have many forms. It can be a liquid, a dry product such as a bar or a powder or a be product having an intermediate moisture content such as a pudding an ice cream or snacks of several forms. It is however preferred to use the liquid form for tube feeding and sip feeding of patients. The product can be nutritionally complete or be a supplemental formula. The product can be a pharmaceutical preparation that is to be consumed simultaneously with or prior to a meal comprising glucose equivalents in order to prepare the body for the uptake of glucose from the blood. In the case the aspartate-rich nutritional or pharmaceutical preparation is to be consumed prior to the meal, it is preferred to consume the preparation at most 60 minutes prior to a meal comprising glucose equivalents, preferably at most 45 minutes, more preferably at most 30 minutes, even more preferably at most 15 minutes, and most preferably at most 10 minutes, especially at most 5 minutes before the meal.

It is preferred that the product is in liquid form. A high osmolarity of the product should be avoided. The osmolarity of the ready to use formula is typically below 500 mOsm/l and preferably 250-400 mOsm/l. Osmolarity of the product can be measured by using standard methods for nutritional products known in the art. Apart from the rapidly available aspartate fraction the remainder of aspartate equivalents in the protein fraction can be somewhat more slowly digestible as is the case when aspartate is present as intact proteins. For taste reasons it is much preferred to use a source of intact protein.

Liquid complete formulae for adults and adolescents are typically designed to provide 2000 kcal per day for a person weighing 70 kg, so about 28 kcal per kg body weight per day. The volume of the formulae to be given is therefore dependent on its energy density. When the product has an energy density of 1.0 kcal per ml, 2 l is required to realise the required daily doses. When the energy density is 1.25 kcal/ml about 1600 ml is required per day.

Typically, the nutritional composition has an energy density of at least 0.95 kcal/ml, preferably at least 1.0 kcal/ml, more preferably at least 1.1 kcal/ml, and a weight ratio of aspartate equivalents to glucose equivalents of 0.046:1-2:1, preferably at least 0.050:1, more preferably at least 0:060:1. However, in case the nutritional composition is to be administered to an infant, the composition preferably has an energy density of less than 0.8 kcal/ml, more preferably less than 0.7 kcal/ml, most preferably less than 0.6 kcal/ml. With the administration of the composition a weight ratio of aspartate equivalents to glucose equivalents of 0.037:1-2:1, preferably at least 0.040:1, more preferably at least 0:045:1 and most preferably at least 0:050:1 is accomplished. Herein, the weight ratio of asp:glucose is based on the amounts of aspartate and glucose equivalents that are present in the composition as well as those given in a meal within 60 minutes after administration of the composition, the numbers being based on the total weight of proteins and carbohydrates, respectively.

For infants the amount of energy that is provided per day is about 540 kcal for an infant that weighs 3 kg, so about 180 kcal/kg body weight per day. This amount of energy rapidly decreases with increasing bodyweight to an amount of about 60 kcal/kg body weight per day after several months of age. When the product is a supplement that supports complete nutrition, and prevents hypo- and hyperglycaemia and/or insulin resistance, the amount of energy that will be provided per day will be in the range of 100-800, preferably 180-600 and more preferably 190-560 kcal. When the product is used as a nutritional or pharmaceutical composition in combination with existing meals, the amount of energy provided will be 10-200 kcal per dose, preferably 15-160 kcal and more preferably 20-140 kcal per dose. This also applies for the case where the product is applied simultaneously with or prior to a meal comprising glucose equivalents.

Infant formulae are defined to be nutritional products intended for complete nutrition of babies or infants from birth to an age of 24 months after birth and that comprise 6-12.5 en % of a protein fraction, 38-50 en % digestible carbohydrates, 40-52 en % of a lipid fraction and all minerals, trace elements and vitamins according to the official recommendations in an amount of 0.8-1.2 times the recommended daily intakes per daily dose and have an energy density of 55-76 kcal per milliliter.

The nutritional composition can comprise at least two separate portions, wherein one portion comprises a protein-rich fraction and a relatively carbohydrate- and fat-poor fraction and another portion comprises relatively a lot of glucose equivalents and less proteins on a weight basis than the first portion, and which portions are administered sequentially and wherein the portion comprising the protein-rich fraction is administered not earlier than 60 minutes before administration of a carbohydrate-rich fraction. Preferably the time between the administration of the protein-rich fraction and the carbohydrate-rich fraction is less than 45 minutes, preferably less than 30 minutes, more preferably less than 15 minutes, even more preferably less than 10 minutes and most preferably less than 5 minutes, wherein the portion comprising the protein-rich fraction is given first. The two portions together satisfy the aforementioned criteria of the nutritional product of the invention.

In the case of sequential administration, it is preferred that the protein level in the first portion is typically larger than the amount of digestible carbohydrates in terms of energy. Typically the protein level is 40-80 en % in the first portion, whereas the carbohydrate fraction in the first portion is lower than 60 en %, preferably lower than 50 en %, most preferably lower than 40 en % based on the total energy content of the first portion. In liquid formulae this first portion will comprise 8-10 wt % protein fraction and the amount of digestible carbohydrates 5-15 wt %, preferably 6-12 wt %, based on the total weight of the first portion, including the liquid. In relatively dry form the first portion can take the form of a snack or a bar. It is preferred to include dietary fibre in an amount of 3-30 wt % of the dry mass of the first portion.

The second portion can be any regular food product that comprises a glucose source. Typically this second portion will comprise 10-32, preferably 14-30 and more preferably 18-22 en % protein, based on the energy content of the second portion. The carbohydrates contribute 25-70, preferably 30-60, more preferably 34-56, most preferably 38-54 en % of the second portion. The lipid fraction originates for 80-100% from the second portion in the diet, which amounts typically to 20-130 gram lipids.

The contribution of proteins, carbohydrates and lipids to the energy content of a product is calculated by using the methods known in the art, using the factors 4 kcal per gram protein equivalent or digestible carbohydrate equivalent and using the factor 9 kcal per gram lipids which include the phospholipids.

It is preferred that the composition provides more than 1800 kcal. Per day, more preferably 1900-2500 kcal/day, preferably about 2000 kcal/day for adults and adolescents. If the composition is used for administration to premature infants, the composition provides more than 225, preferably 300-1000 kcal/day.

Minerals Etc.

The nutritional composition according to the invention optionally comprises other components than the aforementioned protein, digestible carbohydrate and lipid fractions. Below several components are mentioned, including preferred ingredients and doses.

In those embodiments wherein arginine levels in the protein fraction are relatively low, e.g. below 4.0 wt % and certainly below 3.0 wt % of the protein fraction, it is advised to include L-ornithine and/or L-citrulline in the product. It is preferred that the amount of arginine plus ornithine and any citrulline is at least 3.0, especially at least 4.0 wt % of the protein fraction. It is preferred to use L-ornithine or its equivalents in a ratio L-ornithine/citrulline>1 and preferably >5. The L-isomers are preferred. Recommended amounts are 0.3-5 wt % and preferably 0.5-4 wt %, based on the weight of the protein fraction. The weight ratio of L-ornithine+L-citrulline to L-arginine is in the range 0.07:1-2:1 and preferably 0.12:1-1.2:1. The amount of L-ornithine to L-arginine in the product comprising intact proteins and/or hydrolysed forms thereof will therefore be in the range of 0.11-1.1 and preferably 0.2-0.9. L-ornithine can also be included as an extract from raw ingredients like meat or liver. Suitable forms are also salts, in particular those with organic acids like amino acids for example the aspartate salt, or organic acids like malic acid or citric acid or α-keto-isocaproate (or 2-oxo-isocaproate).

By inclusion of additional L-ornithine and/or L-citrulline or their equivalents, in particular in combination with the supplemented methionine equivalents, endogenous polyamine biosynthesis rate is ensured. Inclusion of additional ornithine or its equivalents into the formula supports renal function in persons suffering from hyperglycaemia or insulin resistance. In order to further increase these effects it is important to include carbonates or bicarbonates in the product. Suitable forms are the salts with metals like sodium, potassium, lithium, magnesium, zinc, iron, copper and calcium. The use of cupric carbonate, calcium carbonate and bicarbonates of sodium, magnesium and potassium is recommended. The pH of the formula must be in the range 6.3-7.1 and preferably in the range 6.4-6.8. The amount of carbonates and bicarbonates, including the counter ion must be in the range of 0.8-10, preferably 1.0-6 g and more preferably 1.2-5 g per 100 g dry mass of the formula.

In patients suffering from insulin resistance or increased levels in blood of glucose, resulting in renal complications or a disorder in kidney function, the levels of biotin must be increased to a level between 40 and 4000 μg/100 ml. Magnesium should be included in a concentration of 4-20 mg/100 ml liquid product according the invention. The protein levels in this embodiment of the invention must be between 10 and 22 energy percent of the composition.

The nutritional products according the invention demonstrate essentially no hormone activity when consumed per orally. Hormone-type components selected from glucagons and steroidal compounds are therefore present in amounts less than 10 mg glucagon per liter product. Levels of steroids are typically below 0.1 ppm and preferably non-detectable.

Where the protein fraction exhibits a weight ratio of serine to glycine of less than 2.3:1, a component selected from the group choline, betaine, dimethylglycine and sarcosine must be included in order to support effectiveness in the treatment of hyperglycaemia and during net insulin resistance, in particular in those patients that suffer also from malnourishment and inflammation. The daily dose of these components should be more than 0.5 g and preferably more than 0.8 g. In a liquid product according the invention the concentration becomes therefore more than 0.025 wt % or preferably 0.032-2, more preferably 0.04-0.4 wt % and most preferably 0.06-0.25 wt. %. In dry products the amount will typically be 0.04-3 wt %. Effectiveness can be established via measurement of circulating markers of inflammation like blood levels of C-reactive protein or of several cytokines.

It is important that the product will not demonstrate extensive maillardation i.e. browning, during manufacture, and in particular during sterilisation. This is achieved by preventing inclusion of components like carnosine next to reducing sugars in liquid products. The weight ratio of L-lysine compared to carnosine in the product is therefore typically larger than 5:1 and preferably larger than 10:1.

Zinc is an essential mineral for persons that suffer from hyperglycaemia and/or insulin resistance. The amount of zinc is typically more than 14 mg, preferably more than 18-40 mg, more preferably 20-35 mg and most preferably 22-30 mg per daily dose. It is important to keep the amount of copper relatively low, e.g. in a weight ratio zinc to copper of 7-16:1, and preferably 8-15:1 and most preferably 9-13:1. Despite the relatively high concentration of zinc in the product, the weight ratio of zinc to L-histidine in the product is, due to the relatively high amount of L-histidine, preferably in the range 0.002:1-0.2:1.

Calcium can be advanaeously be included in an amount of more than 40 mg, preferably 50-200 and more preferably 60-120 mg per 100 ml.

Magnesium can be included in liquid formulae in a dose of 20-60, preferably 25-40 and more preferably 28-35 mg per 100 ml liquid product. Magnesium triphosphate, carbonate and bicarbonate are suitable sources of magnesium for use in liquid formulae.

Sodium levels are typically less than 100, preferably 50-80 and more preferably 55-74 mg per 100 ml liquid product according the invention. The weight ratio of sodium to potassium will be typically 0.3-0.66, preferably 0.4-0.64 and more preferably 0.45-0.62.

Chromium or vanadium should be included in an amount of 1-50 μg per 100 ml liquid product according the invention.

It is important that in complete diets all vitamins, minerals and trace elements are included in sufficient amounts to meet nutritional requirements as for example set by the Food and Drug Administration and at the same time not exceed these recommendations in order to avoid overdoses during longer term and frequent use, except where indicated in the description.

It is preferred to include vitamin B6 in the nutritional composition of the invention. The levels hereof are preferably selected to be at least two times the recommended daily amounts to ensure that a greater part of the population that suffers from hyperglycaemia and/or insulin resistance will react on the protein compositions as claimed.

Pyridoxine, pyridoxamine or pyridoxal or their salts, phosphorylated, glycosylated or other derivatives, either prepared synthetically or isolated from natural sources can be used as suitable sources of vitamin B6 and in particular pyridoxine. It is preferred to include 3.2-100 and preferably 3.5-30 mg of vitamin B6 or a source thereof per daily dose for an adult. The weight amount of vitamin B6 in the formula will be less than the weight amount of aspartate equivalents or magnesium in the product. Typically the amount of vitamin B6 is less than 0.01 times the amount of aspartate equivalents in the product and less than 0.1 times the amount of magnesium. For a complete infant formula, the amount of vitamin B6 is preferably more than 75 μg per 100 kcal, especially 80-120 μg/100 kcal.

It is further recommended to include relatively high levels of pantothenic acid, lipoic acid and biotin. Pantothenic acid should be included in an amount of 12-300, preferably 14-100 and most preferably 18-40 mg per daily dose as acid or its salts or pantethine or pantothenol for an adult. Per 100 ml liquid product according the invention the amounts are therefore 0.6-15, preferably 0.7-5 and most preferably 0.9-2 mg. For a complete infant formula, the preferred amount of pantothenic acid is more than 480 μg, especially 500 μg-2.0 mg. Lipoic acid can be included in an amount of 5-500, preferably 10-300, and most preferably 20-200 mg per daily dose, in forms that are known in the art like the free salt, salts thereof or better tasting derivatives. Per 100 ml of a liquid product according to the invention the amounts are therefore 0.25-25, preferably 0.5-15 and most preferably 1-10 mg lipoic acid. Biotin or vitamin H must be included in an amount of 0.2-50, preferably 0.3-30 and most preferably 0.4-20 mg per daily dose. Per 100 ml liquid product according the invention the amounts are 10 μg-2.5 mg, preferably 15 μg-1.5 mg and more preferably 20 μg-1 mg biotin. Suitable sources are D-biotin or biologically and technologically acceptable salts thereof like known in the art.

Folic acid, salts thereof or methylated derivatives thereof are preferably included in an amount of 300-3000, preferably 350-2000 more preferably 400-1500 and most preferably 500-1200 microgram per daily dose for an adult. Per 100 ml liquid product according the invention the concentration of folic acid is therefore 15, preferably 17.5-100, more preferably 20-75 and most preferably 25-60 microgram. In a complete infant formula, the preferred amount of folic acid is above 18 μg per 100 kcal, especially 19-40 mg per 100 ml.

When the present nutritional product is intended to be administered for treatment of hyperglycaemia or of insulin resistance in the young infant who may suffer from underdeveloped metabolic systems, it is preferred to include also limonene. This compound can be given as pure (R)-(+)-limonene as prepared synthetically or as isolated from fruits like citrus fruits. This isolation is preferably applied via steam distillation. The concentration should be in the range 1-1000 mg per 100 g dry matter of the product Treatment The nutritional composition according to the invention is suitable for regulating plasma glucose concentrations and increasing insulin sensitivity in a mammal in need thereof. In particular those mammals suffering from hyperglycaemia and/or insulin resistance have problems with the control of glucose and/or insulin are considered to be in need of the present composition. These mammals typically suffer from too high a level of glucose and/or insulin, which is often associated with the disorders described in the introduction, in particular with secondary diseases or disorders from the group of cardiovascular diseases, in particular atherosclerosis and microvascular problems, cerebrovascular problems in particular Transient Ischemic Accidents and Cerebro-Vascular Accidents, renal diseases, obesitas, childhood obesitas, imparted eye sight, high blood pressure and loss of tissue or organ function, imparted immune function, dysfunction of the sexual organs, in particular imparted libido, catabolism especially after trauma, surgery or during severe phases in diseases like cancer, infection, gangrene-type problems with limbs, acquired immune distress syndrome, metabolic syndrome, diabetes, increased HbA1C levels, chronic inflammation, chronic obstructive pulmonary disease and liver diseases.

The effect of the product can be determined by measuring the levels of glucose in blood after consumption of the nutritional product according the invention. Consumption of the protein fraction comprising the relatively high amount of rapidly available aspartate will decrease postprandial or post-surgery glucose levels as observed after consumption of a glucose source. This is particularly the case when the aspartate is more rapidly available to the organism than the glucose source. In particular the slow release system of the carbohydrate fraction as disclosed ensures a more slow availability of the dietetic glucose compared to the aspartate. Another way of achieving this effect is through sequential administration of separate protein and digestible carbohydrate fractions, wherein the protein fraction is administered prior to the carbohydrate fraction. Clearance rate of glucose and insulin (t ½) can be monitored as well as the effect on steady state glucose and insulin levels. The effectiveness of the dietetic regimen becomes for example clear from the number of times a hypoglycemic state (blood glucose below 50 mg/100 ml) occurs, in combination with the number of times a hyperglycemic state occurs.

The effectiveness of the inclusion of the amino acids as specified in the description can be determined by measuring loss in lean body mass in persons that suffer from hyperglycaemia and insulin resistance and in particular in malnourished diabetic patients.

The effect of the inclusion of the vitamins as specified in the description can be determined by measuring rate of lipolysis, insulin resistance and lean body mass in obese persons that suffer from hyperglycaemia and/or insulin resistance.

Risk for complications can be monitored by measuring the decrease in blood levels of HbA1c and/or C-reactive protein. Incidence of typical complications like cardiovascular problems can be tabulated. In persons that suffer from hyperglycaemia and/or insulin resistance and additional renal problems blood ammonia levels should be measured.

In persons suffering from increased insulin resistance due to increased release of stress hormones plasma glucose levels and changes in lean body mass after experiencing of e.g. the trauma or severe surgery should be measured, including the morbidity and mortality.

It is important to extend the measurements to a period of 2 days or longer in order to allow adaptation of the organism to the dietetic protein composition. The effect thereafter can however be immediate or on longer term, dependant on the patient.

EXAMPLES

Example 1

Complete Liquid Nutritional Product for Diabetic Patients Suffering from High Postprandial Glucose Plasma Levels and/or Insulin Resistance

| Liquid composition that comprises per 100 ml: | |
| --- | --- |
| Energy: | 1.08 kcal/ml |
| Protein: | 5.5 g (=22 kcal = 20.4 en %) |

(its contents given below)

| Lipids: 4.0 g (=36 kcal = 33.3 en %) | |
| --- | --- |
| Marine oil | 0.4 g |
| Rapeseed oil | 1.2 |
| MCT oil | 0.3 |
| Olive oil | 0.8 |
| Linseed oil | 0.5 |
| Phospholipids | 0.8 |

| Carbohydrates: 12.5 g (=50 kcal = 46.3 en %) | |
| --- | --- |
| Isomaltulose oligomer | 4 g |
| Glucose oligo/polymer | 6 g |
| Galactose oligomer | 0.5 g |
| Maltose | 0.3 |
| Lactose | 1.7 g |

| Fiber 1 g | |
| --- | --- |
| From hydrolysed guar | 0.2 g |
| From inulin | 0.7 g |
| From galactose | 0.1 g |

| Micro-ingredients | | | |
| --- | --- | --- | --- |
| Na | 100 mg | K | 150 mg |
| Cl | 125 mg | Ca | 80 mg |
| P | 72 mg | Mg | 23 mg |
| Fe | 1.6 mg | Zn | 3.0 mg |
| Cu | 0.25 mg | Mn | 0.33 mg |
| F | 0.1 µg | Mo | 15 µg |
| Se | 5.7 µg | Cr | 6.7 µg |
| I | 13 µg | | |
| Vit A | 82 µg RE | Vit D | 0.7 µg |
| Vit E | 1.3 mg α-TE | Vit K | 10 µg |
| Vit B1 | 0.2 mg | Vit B2 | 0.16 mg |
| Niacin | 1.8 mgNE | Pantothenic acid | 1.3 mg |
| Vit B6 | 0.6 mg | Folic acid | 40 µg |
| Biotin | 40 µg | Choline | 37 mg |
| Vit C | 10 mg | | |

The protein fraction of the above liquid composition is one of the following:

Example 1a

| Soy | 5 g |
| --- | --- |
| L-aspartic acid | 0.5 g |

Example 1b

| Soy | 4 g |
| --- | --- |
| alpha-lactalbumin enriched whey (aLW) | 1.5 g |

Example 1c

| Soy protein hydrolysate | 2 g |
| --- | --- |
| alpha-lactalbumin enriched whey (aLW) | 3.5 g |

Example 1d

| hydrolysed soy protein | 3.5 g |
| --- | --- |
| alpha-lactalbumin enriched whey (aLW) | 1.9 g |
| L-methionine | 0.1 g |

Example 1e

| hydrolysed soy protein | 2 g |
| --- | --- |
| potato protein hydrolysate | 3 g |
| L-lysine | 0.2 g |
| L-methionine | 0.2 g |
| L-serine | 0.1 g |

Example 2

Complete Nutrition for Intensive Care Unit Patients

Energy density is 1.25 kcal/ml
The nutrition comprises per 100 ml:
  Protein: 7.5 g=24 en %
  Casein 3.1 g
  Alpha-lactalbumin enriched whey 3.7 g
  L-aspartic acid 0.8 g
  L-ornithine 0.3 g
  L-leucine 0.2 g
  L-glutamine 0.9 g
  Carbohydrates: 14.5 g=46 en %
  Maltodextrins 12 g
  Fructose 0.3 g
  Galactose 1 g
  Glucose and other sugars 1.2 g
  Fats: 4.2 g=30 en %
  Monounsaturated 2.8 g
  Saturated 0.4 g
  Polyunsaturated 1.0 g
  ω-3/ω-6 weight ratio in LC-PUFA's =1-10
  Dietary fiber: 1.6 g
  Low methoxylated pectin 0.2 g
  Wheat bran: 0.2 g
  Other 1.2 g

| Microingredients: As RDI | | |
| --- | --- | --- |
| Na: | 134 mg | vitamin A |
| K | 263 mg | vit. D |
| Cl | 139 mg | vit. E |
| Ca | 67 mg | vit. K |
| P | 67 mg | vit. B1 |
| Mg | 28 mg | vit. B2 |

-continued

| Microingredients: As RDI | | |
| --- | --- | --- |
| Fe | 1 mg | niacin |
| Zn | 1.4 mg | pantothenic acid |
| Cr | 10 μg | vit. B6 |
| F | 0.1 mg | folic acid |
| Cu | 0.3 mg | |
| Se | 0.02 mg | biotin |
| Mo | 0.01 mg | vit. C |
| I | 0.02 mg | |

Betain: 0.4 g
Acetyl-1-carnitine: 0.02 g
Myo-inositol: 0.1 g

Example 3

Complete Nutritional Product for Infants to Prevent Childhood Obesity

The product comprises per 100 ml:
Protein: 1.4 g (yielding 0.16 g aspartate (=11.4 wt %), 0.307 g glutamate and weight ratio of asp/glu ratio of 0.52)
Whey enriched in alpha-lactalbumin: 1.12 g
Hydrolysed soy protein isolate: 0.28 g

| | |
| --- | --- |
| Carbohydrates | 8.9 g |
| Lactose | 5 g |
| Maltodextrins/glucose syrup | 3.9 g |

| Lipids: | |
| --- | --- |
| Marine oil | 3.1 g |
| Egg lecithin | 0.4 g |
| Milk fat | 0.6 g |
| Randomised oil | 0.2 g |
| Rapeseed | 0.4 g |
| Olive oil | 0.8 g |
| | 0.7 g |

| Microingredients | | | |
| --- | --- | --- | --- |
| Na | 23 mg | K | 66 mg |
| Cl | 50 mg | Ca | 45 mg |
| P | 23 mg | Mg | 6 mg |
| Fe | 0.53 mg | Zn | 0.8 mg |
| Cu | 0.09 mg | Se | 1.5 μg |
| I | 12 μg | | |
| Vitamin A | 84 μg RE; | vitamin D | 1.4 μg; |
| Vitamin E | 0.8 mg alpha TE; | vitamin K | 4.9 μg; |
| Vitamin B1 | 0.1 mg; | vitamin B2 | 0.1 mg; |
| Niacin | 1.2 mg NE; | pantothenic acid | 0.8 mg; |
| Vitamin B6 | 0.06 mg; | folic acid | 15 μg; |
| Biotin | 3 μg; | vitamin C | 8 mg; |
| Taurine | 10 mg | | |

Example 4

Pharmaceutical Product for Use Prior to a Meal

Bar of 10 g providing:
  4 g dried mashed meat puree;
  1.7 g alpha-lactalbumin enriched whey protein;
  0.3 g L-aspartic acid;
  3 g matrix consisting of a carbohydrate fraction including a glucose syrup and about 1 g of gums that solidify the product and about 0.7 g of wheat bran; and
  1 g herbs, spices, minerals, and additives

Example 5

Dried Soup for Reconstitution in Boiling Water for Use Prior to a Meal

The soup comprises per 20 g dried product:
  10 g dried and mashed meat
  1 g L-aspartic acid
  0.5 g thickener (gums)
  6.5 g dried vegetables and herbs
  2 g ash, including sodium chloride

Example 6

Dry Product (e.g. a Bar Bon-bon or Candy) for Use Prior to a Normal Meal

Example 6a

Snack in the form of a friable product providing per 100 g dry matter 75 g protein, 12 g lipids, 8 g carbohydrates, 3 g dietary fiber (wheat bran) and 5 g minerals, trace elements and vitamins using meat extract, potato protein, egg lecithin, minerals, trace elements, vitamins and spices.

Example 6b

Sausage manufactured by using proteins from pea/soy/fish/lupine/meat/liver or potato, low methylated pectin, egg-lecithin, maltodextrins and spices and minerals that comprises per 100 g dry matter: 60 g proteins, 20 g lipids, 8 g dietary fiber, 8 g carbohydrates and 4 g minerals, trace elements and spices.

Example 6c

Bar of 30 g Comprising Per 100 g Dry Matter 35 g protein, 40 g carbohydrates, 5 g dietary fiber, 10 g lipids and 10 g minerals, trace elements and vitamins using potato protein, lupine protein, maltodextns, wheat bran, fruits, egg lecithin and synthetic vitamins, minerals and trace elements.

The snack, sausage or bar is the first portion. In combination with a second portion which could be one or more liquid or dry nutritional products, a total of 15-22 en % protein, 45-55 en % carbohydrates and 30-40 en % lipids is administered.

Example 7

Beneficial Effect of Aspartate-rich Protein Fraction on the Blood Glucose Level

The effect of aspartate on the blood glucose level after the uptake of food was tested by administering a food rich in aspartate to a group of 8 rats and measuring blood levels of glucose at various times. Canules were applied in the stomach, for controlled administration of the food, and in the heart for taking blood samples before and after administration of the food. At time zero a bolus dose was given of either glucose alone or the same amount of glucose and a fixed amount of protein fraction. The dose was 2.5 g protein fraction per kilogram body weight and 1 g glucose per kg body weight. The rats weighed about 300 g.

Figure 1:
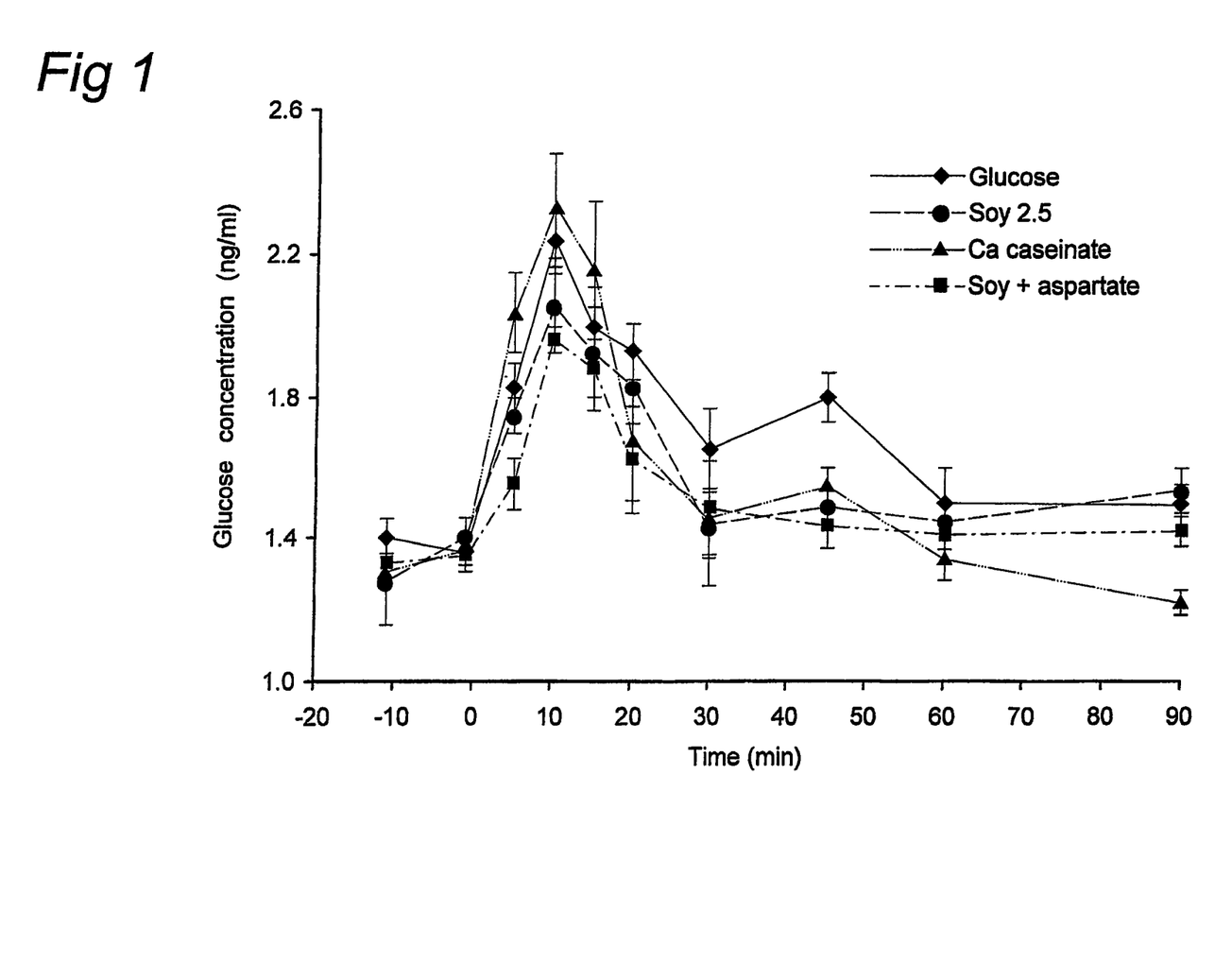
Figure 2:
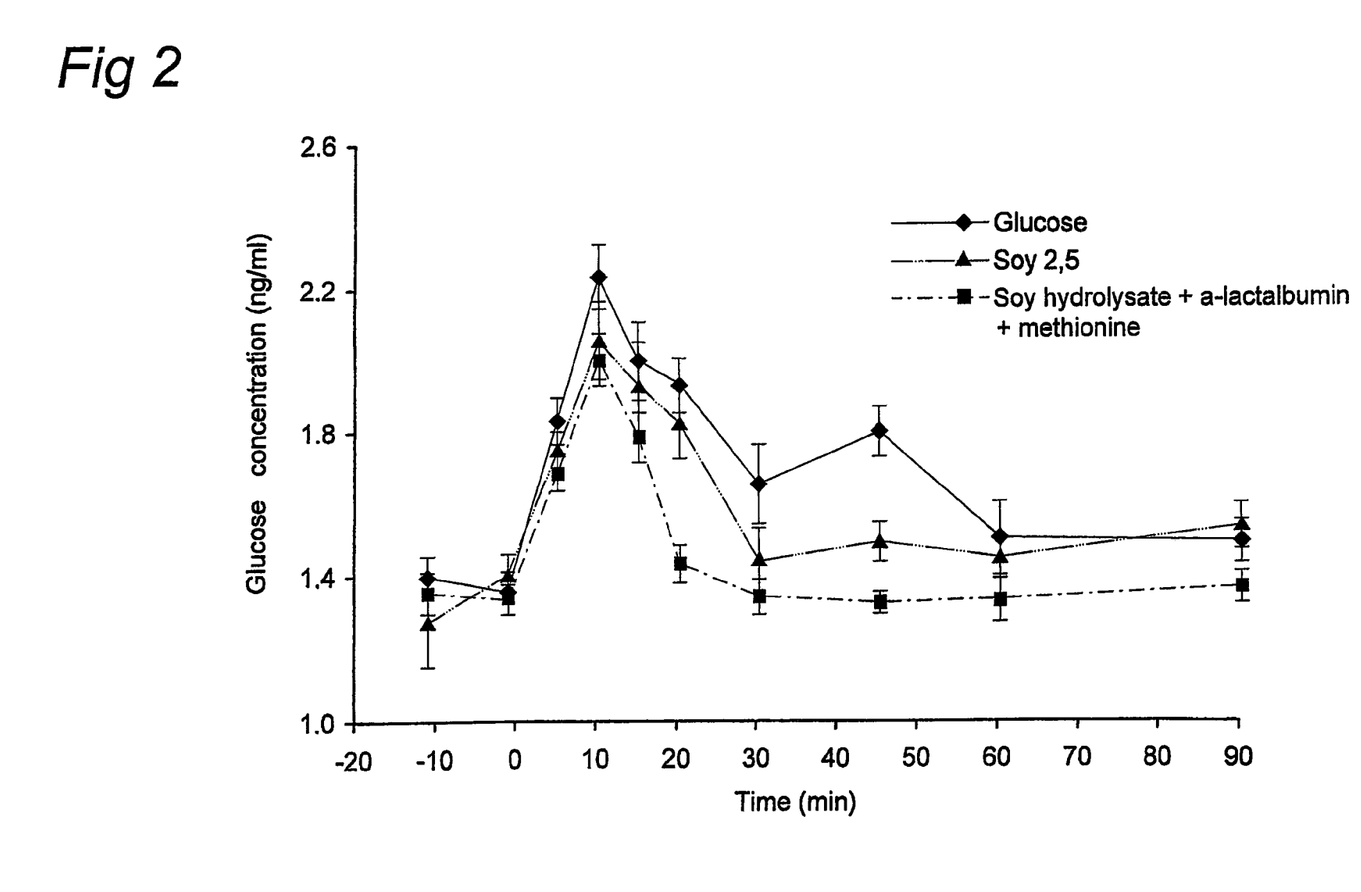

In FIGS. 1 and 2 the glucose response is plotted in time. FIG. 1 shows that the glucose levels reach lower peak values upon administration of more aspartate equivalents; the maximum glucose concentration drops from 2.5 g caseinate (7.8 wt % aspartate equivalents), 2.5 g. soy (10.8 wt % aspartate equivalents) to soy enriched with aspartate equivalents. The nutritional composition comprising a mixture of soy hydrolysate and alpha-lactalbumin, and further supplemented with methionine enhances the uptake of glucose from the blood plasma in comparison with the effects achieved for 2.5 g soy (see FIG. 2). Moreover, both figures show that the aspartate-enriched foods make flattening of the glucose levels in blood after the uptake of food comprising glucose occur faster.

The invention claimed is:

1. A method for regulating plasma glucose concentrations and/or increasing insulin sensitivity in a mammal in need thereof, said method comprising the steps of administering to said mammal a nutritional or pharmaceutical composition comprising 10-30 energy % of a protein fraction, wherein said protein fraction comprises a first source of aspartate equivalents selected from the group consisting of a protein, isolate, concentrate, and hydrolysate thereof comprising L-aspartic acid and/or L-asparagine, and wherein the protein fraction comprises at least 10.8 wt % aspartate equivalents, based on the weight of the protein fraction.

2. The method according to claim 1, wherein said protein fraction comprises a second source of aspartate equivalents selected from the group consisting of a protein, isolate, concentrate, and hydrolysate thereof comprising L-aspartic acid and/or L-asparagine.

3. The method according to claim 1, wherein said protein is a lactalbumin-enriched whey or a potato protein.

4. The method according to claim 1, wherein said protein fraction further comprises glutamate equivalents in a weight ratio of aspartate equivalents to glutamate equivalents (asp: glu) between 0.41:1 and 5:1.

5. The method according to claim 4, wherein the weight ratio of asp:glu is between 0.58:1 and 2:1.

6. The method according to claim 1, wherein said protein fraction comprises a protein of animal origin selected from the group consisting of meat or liver of a mammal, and milk whey, and a protein from plants selected from the group consisting of soy, lupin, pea, potato, and bean.

7. The method according to claim 1, wherein the aspartate equivalents are administered simultaneously with, or at most 60 minutes prior to, a meal comprising glucose equivalents.

8. The method according to claim 1, wherein the nutritional composition further comprises a carbohydrate fraction comprising 40-100 wt % glucose equivalents.

9. The method according to claim 8, wherein the nutritional composition comprises at least two separate portions, wherein a first portion comprises at least a part of the protein fraction, said part comprising at least 10.8 wt % of aspartate equivalents, and a second portion comprises at least a part of the carbohydrate fraction, and wherein said first portion is administered simultaneously with, or at most 60 minutes prior to, the second portion comprising the carbohydrate fraction.

10. The method according to claim 8, wherein said carbohydrate fraction comprises oligosaccharides that comprise more than 50 wt % glucose and that have a chain length of 3-9.

11. The method according to claim 8, wherein the nutritional composition comprises at least two separate portions, wherein a first portion comprises at least a part of the protein fraction, said part comprising at least 10.8 wt % of aspartate equivalents, and a second portion comprises at least a part of the carbohydrate fraction, and wherein said first portion is administered simultaneously with, or at most 60 minutes prior to, the second portion comprising the carbohydrate fraction.

12. The method according to claim 8, wherein the aspartate equivalents are administered in an amount corresponding with a weight ratio of aspartate equivalents to said glucose equivalents of 0.037:1-2:1, wherein the amounts of aspartate and glucose equivalents are the sum of those present in the composition and in any meal administered within 60 minutes from administering the composition or a first part thereof.

13. The method according to claim 12 for administration to an infant, wherein the nutritional composition has an energy density of less than 0.8 kcal/ml.

14. The method according to claim 12, wherein the nutritional composition has an energy density of at least 0.95 kcal/ml and a weight ratio of aspartate equivalents to glucose equivalents of 0.046:1-2:1, wherein the amounts of aspartate and glucose equivalents are the sum of those present in the composition and in the meal.

15. The method according to claim 1, wherein the method is used for treating and/or reducing hyperglycemia and/or insulin resistance.

16. The method according to claim 1, wherein said mammal is suffering from one or more secondary diseases or disorders selected from the group consisting of glucose intolerance, insulin resistance, cardiovascular disease, atherosclerosis, microvascular disease, cerebrovascular disease, transient ischemic attacks, renal diseases, obesity, childhood obesity, impaired eyesight, high blood pressure, loss of tissue or organ function, impaired immune function, dysfunction of the sexual organs, impaired libido, catabolism, catabolism after trauma, surgery, cancer, infection, gangrene in limbs, acquired immune deficiency syndrome, diabetes, increased HbA1C levels, chronic inflammation, chronic obstructive pulmonary disease and liver disease.

17. The method according to claim 1, wherein the protein fraction comprises less than 4.0 wt % arginine, wherein the protein fraction further comprises at least one of ornithine and citrulline, and wherein the amount of arginine, ornithine and citrulline is at least 4.0 wt %, based on the weight of the protein fraction.

18. A method for regulating plasma glucose concentrations and/or increasing insulin sensitivity in a mammal in need thereof, said method comprising the step of administering to said mammal a nutritional or pharmaceutical composition comprising a protein fraction comprising 12.0-40 wt % of aspartate equivalents, based on the total weight of the protein fraction, wherein said aspartate equivalents are selected from the group consisting of a protein, isolate, concentrate, and hydrolysate thereof comprising L-aspartic acid and/or L-asparagine.

19. A method for regulating plasma glucose concentrations in a mammal in need thereof, said method comprising the steps of administering to said mammal a nutritional or pharmaceutical composition comprising a protein fraction comprising at least 10.8 wt % aspartate equivalents based on the weight of the protein fraction, wherein said aspartate equivalents are selected from the group consisting of a protein, isolate, concentrate, and hydrolysate thereof comprising L-aspartic acid and/or L-asparagine.

20. A method for regulating plasma glucose concentrations in a mammal in need thereof, said method comprising the step of administering to said mammal a nutritional or pharmaceutical composition comprising a protein fraction comprising 12-40 wt % of aspartate equivalents, based on the total weight of the protein fraction, wherein said aspartate equivalents are selected from the group consisting of a protein, isolate, concentrate, and hydrolysate thereof comprising L-aspartic acid and/or L-asparagine.

* * * * *

UNITED STATES PATENT AND TRADEMARK OFFICE
CERTIFICATE OF CORRECTION

PATENT NO. : 8,501,676 B2
APPLICATION NO. : 11/632871
DATED : August 6, 2013
INVENTOR(S) : Robert Johan Joseph Hageman It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1374 days.

Signed and Sealed this
Fifteenth Day of September, 2015

Michelle K. Lee
*Director of the United States Patent and Trademark Office*